United States Patent

Makino et al.

Patent Number: 5,612,327
Date of Patent: Mar. 18, 1997

[54] 1α,24-(OH)$_2$-CHOLECALCIFEROL EMULSION COMPOSITION AND METHOD FOR TREATING PSORIASIS

[75] Inventors: Yuji Makino; Hideo Matugi; Yoshiki Suzuki, all of Hino, Japan

[73] Assignee: Teijin Limited, Osaka, Japan

[21] Appl. No.: 428,106

[22] PCT Filed: Sep. 1, 1994

[86] PCT No.: PCT/JP94/01443

§ 371 Date: Apr. 28, 1995

§ 102(e) Date: Apr. 28, 1995

[87] PCT Pub. No.: WO95/06482

PCT Pub. Date: Mar. 9, 1995

[30] Foreign Application Priority Data

Sep. 1, 1993 [JP] Japan ..................... 5-217261

[51] Int. Cl.$^6$ ........................ A61K 47/44
[52] U.S. Cl. ........................ 514/167
[58] Field of Search ................. 514/167

[56] References Cited

U.S. PATENT DOCUMENTS 4,871,723  10/1989  Makino et al. ............ 514/167

FOREIGN PATENT DOCUMENTS 26223    4/1987  Japan.
223163  10/1987  Japan.
9414453  7/1994  WIPO.

OTHER PUBLICATIONS

CA 105: 30074, Makino, 1986.

*Primary Examiner*—Rebecca Cook
*Attorney, Agent, or Firm*—Sughrue, Mion, Zinn, Macpeak & Seas

[57] ABSTRACT

A 1α,24-(OH)$_2$—V.D$_3$ cream composition comprising (a) a therapeutically effective amount of 1α,24-(OH)$_2$—V.D$_3$, (b) an oil phase component including (i) a solid oil component composed of 5 to 20 parts by weight of white petrolatum and 5 to 15 parts by weight of higher alcohols and (ii) a liquid oil component comprising of 3 to 10 parts by weight of squalane, (c) an aqueous phase component, and (d) 2.5 to 7.5 parts by weight at least two surfactants, wherein the 1α,24-(OH)$_2$—V.D$_3$ cream composition has a weight ratio of the solid oil component to the liquid oil component (i.e., solid oil component/liquid oil component) of at least approximately 2, the higher alcohols are composed of stearyl alcohol and cetyl alcohol, the weight ratio of the stearyl alcohol to the higher alcohols (i.e., stearyl alcohol/higher alcohols) is approximately 0.65 to approximately 0.9, at least 50% by weight of the surfactants is at least one surfactant having an HLB value of approximately 5 or less, and the HLB value of the surfactants as a whole is approximately 8 to approximately 18.

6 Claims, 1 Drawing Sheet

1α,24-(OH)$_2$-CHOLECALCIFEROL EMULSION COMPOSITION AND METHOD FOR TREATING PSORIASIS

TECHNICAL FIELD

This is a 371 of PCT/JP94/01443 filed Sep. 1, 1994.

The present invention relates to a novel 1α,24-(OH)$_2$—V.D$_3$ cream composition. More specifically, the present invention relates to a 1α,24-(OH)$_2$—V.D$_3$ cream composition having a good skin permeability of the active ingredient 1α,24-(OH)$_2$—V.D$_3$. Still more specifically, the present invention relates to a 1α,24-(OH)$_2$—V.D$_3$ cream composition having a good skin permeability of the active ingredient 1α,24-(OH)$_2$—V.D$_3$, having an improved chemical stability of the active ingredient 1 α,24-(OH)$_2$—V.D$_3$, superior in physical stability as a cream composition, and superior in feeling at the time of application to the skin.

BACKGROUND ART

1α,25-(OH)$_2$—V.D$_3$ (1α,25-dihydroxylcholecalciferol), 1α,24-(OH)$_2$—V.D$_3$ (1α,24-dihydroxylcholecalciferol), etc. exhibit a Ca-homeostasis regulating action, which is known as a biological action of V.D$_3$, and therefore, are called active-type V.D$_3$s. The biological actions of active type V.D$_3$s are diverse. In addition to the above-mentioned Ca-homeostasis regulating action, mention may be made of an action of bone formation, an action of inducing cell differentiation, an action of suppressing the secretion of the para-thyroid hormone, etc. Among these, regarding the Ca-homeostasis regulating action, the above substances are already being clinically administered as oral formulations for treatment of osteoporosis, osteomalacia, and other so-called osteopenia and are recognized to have superior therapeutic effect. On the other hand, clinical application has been studied for the action in inducing cell differentiation, though later than with the Ca-homeostasis regulating action. In particular, since the hard-to-cure skin disease of psoriasis is considered to be caused by the incomplete undifferentiation and accelerated proliferation of epidermic cells, application of active-type V.D$_3$s has been studied. As psoriasis is a disease of the epidermis, the outer layer of the skin, local administration to the affected location of the skin is more advantageous over oral administration, injection, and other general administration in terms of bioavailability and also enables prevention of general side effects, and is therefore considered as a best method of administration.

Dosage forms for local skin administration include ointments, creams, and other semisolid agents, tape agents, cataplasms, powder agents, etc., but when considering the symptoms of psoriasis, semisolid agents are best. As a 1α,24-(OH)$_2$—V.D$_3$ ointment, the present inventors have already disclosed a formula for an water-free ointment (see the specification of Japanese Examined Patent Publication (Kokoku) No. 3-68009). Good therapeutic effects have been reported by this water-free ointment, but since the base of the ointment is white petrolatum, it is not possible to avoid an oily, sticky feeling after application. Therefore, there has been a need for an external formulations improved in the feeling when applied onto the face etc.

Cream compositions include large amounts of water, and therefore, are not sticky as with ointments and have been used for a long time as external agents. They are classified by composition into two types of emulsion type cream compositions, that is, oil-in-water types (O/W) or water-in-oil types (W/O), as well as aqueous gel type cream compositions. A comparison of these three types by the state when rubbed on the skin shows that the aqueous gel type cream compositions suffer from the problem of the gel base polymer precipitating on the skin, while the water-in-oil type (W/O) emulsion cream compositions suffer from the problem that the white color and other external colors do not easily vanish. As opposed to this, oil-in-water type (O/W) emulsion cream compositions are advantageous in that the white color and other external colors easily vanish.

However, in the case of psoriasis, in particular, since it occurs mostly on the face, an oil-in-water type emulsion cream composition has been desired which not only enables the external color to vanish, but also which does not stand out at the applied location, in particular does not shine at the applied location, and therefore, feels good upon application.

Oil-in-water type emulsion cream compositions are composed of an oil phase consisting of a solid oil component which is normally mainly solid or semisolid at ordinary temperature and a liquid oil component which is liquid at ordinary temperature, an aqueous phase including propylene glycol or glycerine or another humectant etc., a surfactant, etc. (For general technology regarding these cream compositions, see for example "Shin Keshohingaku" (New Cosmetic Science), edited by Takeo Mitsui, 1993, Nanzando.)

As the above-mentioned solid oil component, normally use is made of white petrolatum, solid paraffin, and other hydrocarbons; cetyl alcohol, stearyl alcohol, and other higher alcohols; palmitic acid and other higher fatty acids; beeswax, carnauba wax, and other waxes (esters); and lanolin and other sterol esters and as the above-mentioned liquid oil component, liquid paraffin, squalane, and other hydrocarbons; medium chain-length fatty acid triglyceride, almond oil, olive oil, diisopropyl adipate, and other esters etc. (Dermatological Formulation: B. W. Barry, Marcel Dekker Co., 1983).

Further, as the above-mentioned surfactant, many non-ionic surfactants and ionic surfactants are used alone or in combinations with two types or more. For emulsification of an oil-in-water type emulsion, the HLB value of the surfactant is, in general, said to be suitably in the range of approximately 8 to approximately 18. (For example, see "Bunsan Nyukakei no Kagaku" (Chemistry of Dispersions and Emulsions), Kitahara et al, 1988 Kogaku Tosho, p. 63.)

Several prior arts have already been disclosed for cream compositions of active-type V.D$_3$s.

For example, the specification of EP-A-0,129,003 discloses a cream composition of 1α-OH—V.D$_3$ or 1α,25-(OH)$_2$—V.D$_3$ and describes a cream composition formula of 20 parts by weight of beeswax as the solid oil component and 40 parts by weight of liquid paraffin and 1 part by weight of almond oil as the liquid oil component. Further, the specification of Japanese Unexamined Patent Publication (Kokai) No. 60-174705 discloses a cream composition of 1α,25-(OH)$_2$—V.D$_3$ and describes a cream composition formula including a solid oil component comprising petrolatum, beeswax, higher fatty acids, etc. and a liquid oil component comprising liquid paraffin, squalane, etc.

Further, the specification of Japanese Unexamined Patent Publication (Kokai) No. 4-210903 discloses an emulsion-type local administered medicinal composition of 1α,25-(OH)$_2$—V.D$_3$, describes a cream composition formula including cetyl alcohol, stearyl alcohol, and other solid oil components (NOTE: the specification describes them as viscosity adjusters) and liquid paraffin and other liquid oil components (NOTE: the specification describes them as lyophilic solubilizers) etc., and states that the chemical stability of the 1α,25-(OH)$_2$—V.D$_3$ in the 1α,25-(OH)$_2$—V.D$_3$ emulsion composition is achieved by adjusting the pH to approximately 6.5 to approximately 7.5.

Further, the specification of WO92/01454 and the specification of WO91/1280 disclose cream compositions of recalcipotriol or a 20(R)-22-oxa-V.D$_3$ derivative and describes a cream composition formula including a solid oil component comprising white petrolatum, stearyl alcohol, and the like and a liquid oil component comprising liquid paraffin.

These illustrated cream compositions or emulsion compositions are comprised of components used for normal cream composition preparations. (For example, see the above-mentioned book of Barry.) As a feature of the components or proportions deserving special mention, it was stated in the specification of Japanese Unexamined Patent Publication (Kokai) No. 4-210903 that the pH should be controlled to approximately 6.5 to approximately 7.5 for stabilization of the active ingredient, but nothing further was touched upon. That is, nothing particular was observed regarding the components making up the oil phase or the components of the surfactant.

The present inventors, however, engaged in intensive studies of various types of cream compositions prepared in accordance with the technology disclosed above with the intention of producing a cream composition of 1α,24-(OH)$_2$—V.D$_3$, which is one of active-type V.D$_3$, and as a result, ran into the problems that (1) in the prior art, it was not possible to obtain sufficient skin permeability of the active ingredient 1α,24-(OH)$_2$—V.D$_3$ or to achieve a superior pharmacological effect in animal tests (in particular, these were worse than the ointment of the present inventors (see specification of Japanese Examined Patent Publication (Kokoku) No. 3-68009), (2) in the prior art, there was room for improvement of the chemical stability of the active ingredient 1α,24-(OH)$_2$—V.D$_3$, (3) some of the cream compositions made by the previously disclosed technology were found to be insufficient in terms of physical stability, and (4) some of the cream compositions made by the previously disclosed technology were found to be insufficient in terms of the feeling, such as stickiness upon application to the skin or shininess of the applied location.

Namely, in the 1α,24-(OH)$_2$—V.D$_3$ cream compositions made using 1α,24-(OH)$_2$—V.D$_3$ as the active ingredient in accordance with formulas disclosed in the specification of EP-A-0,129,003, the specification of Japanese Unexamined Patent Publication (Kokai) No. 60-174705, the specification of Japanese Unexamined Patent Publication (Kokai) No. 4-210903, and the specifications of WO92/01454 and WO91/1280, both the skin permeability and the pharmacological effect of the 1α,24-(OH)$_2$—V.D$_3$ were inferior to the ointment of the present inventors (see specification of Japanese Examined Patent Publication (Kokoku) No. 3-68009) and there was room for improvement in the chemical stability as well.

Further, the formulas disclosed in the specification of EP-A-0,129,003 and the specification of Japanese Unexamined Patent Publication (Kokai) No. 60-174705 suffered from the problems of stickiness at the time of coating, shininess of the applied location, and physical stability, i.e., easy separation of the oil phase and water phase under heating or under contrifugation. Further, in the formula disclosed in the specification of Japanese Unexamined Patent Publication (Kokai) No. 4-210903, there was the problem of physical stability, i.e., the easy separation of the oil phase and aqueous phase under heating or contrifugation.

In the formula illustrated in WO92/01454 and 91/1280, shininess of the applied location could not be eliminated.

That is, while these disclosed prior art did give several examples of formulas of active-type V.D$_3$ emulsion compositions (e.g., cream compositions), the skin permeability and pharmacological activity and the chemical stability of the 1α,24-(OH)$_2$—V.D$_3$ were insufficient and the physical stability of the cream composition and the feeling upon application were not necessarily satisfactory either.

DISCLOSURE OF THE INVENTION

The problem to be solved by the present invention is to provide a 1α,24-(OH)$_2$—V.D$_3$ cream composition having the improved skin permeability of the active ingredient 1α,24-(OH)$_2$—V.D$_3$ and as a result, exhibiting a sufficient pharmacological effect and improved chemical stability. Further, it is to simultaneously provide a 1α,24-(OH)$_2$—V.D$_3$ cream composition having the improved physical stability and feeling upon application.

The present inventors engaged in intensive research to solve the above-mentioned problem and, as a result, clarified for the first time that the skin permeability of the active ingredient 1α,24-(OH)$_2$—V.D$_3$ is dependent on the components of the cream composition, more particularly the types and proportions of the oil phase component, and that the chemical stability of the 1α,24-(OH)$_2$—V.D$_3$ in the cream composition is largely dependent on the types and proportions of the surfactants, and discovered that the physical stability of the cream composition is dependent on the ratio of the solid oil component to the liquid oil component in the oil phase and that the feeling at the time of application are deeply related to the type of the liquid oil component in particular, and thereby completed the present invention. The background leading up to the above discoveries and the technical concept of the invention will be explained below:

Regarding the first feature of the skin permeability, in general, to raise the skin permeability of the active ingredient in a cream composition, it is desirable to include the active ingredient in the cream composition in a concentration as close to saturated solubility as possible, but 1α,24-(OH)$_2$—V.D$_3$ is chemically unstable and does not dissolve much at all in a non-polar solvent, and therefore, when following the formula for a normal cream composition, it is extremely difficult to ensure the stable presence of 1α,24-(OH)$_2$—V.D$_3$ in a concentration close to saturation.

On the other hand, it is known to use as the solid oil component of the cream composition, for example, a mixture of cetyl alcohol, stearyl alcohol, or cetostearyl alcohol or other higher alcohols and hydrocarbons.

Surprisingly, however, the present inventors discovered that, when using a mixture of higher alcohols and white petrolatum as the solid oil component and squalane as the liquid oil component, the skin permeability of the 1α,24-(OH)$_2$—V.D$_3$ was remarkably dependent on the composition. That is, the present inventors discovered that the skin permeability of the active ingredient 1α,24-(OH)$_2$—V.D$_3$ depends on the types and proportions of the oil phase component and that, for example, when the weight ratio of the stearyl alcohol to the cetyl alcohol was changed to compare the skin permeability of the 1α,24-(OH)$_2$—V.D$_3$, the permeability suddenly increases when the ratio of stearyl alcohol becomes over approximately 70%. Further, the present inventors discovered that the increase in the skin permeability was reflected as well in the pharmacological effect of the 1α,24-(OH)$_2$—V.D$_3$ in psoriasis model animals and that when the ratio of stearyl alcohol becomes over approximately 65%, in particular approximately 70%, a pharmacological effect equivalent to the water-free ointment previously proposed and commercialized by the present inventors was exhibited.

Second, regarding the factors behind the chemical stability of the active ingredient $1\alpha,24\text{-(OH)}_2\text{—V.D}_3$, the present inventors discovered that having as much of the $1\alpha,24\text{-(OH)}_2\text{—V.D}_3$ distributed in the oil phase as possible was important in the long term chemical stability and that, therefore, the types and proportions of the surfactants were important as factors governing the rate of distribution in the oil and aqueous phases of the $1\alpha,24\text{-(OH)}_2\text{—V.D}_3$ in addition to the types and proportions of the oil phase component.

That is, they discovered that having at least 50% by weight or more of the surfactants, constituting the 2.5 to 7.5 parts by weight of the cream composition of the present invention, be surfactants having an HLB value of about 5 or less and having the HLB value of the surfactants as a whole be approximately 8 to approximately 18, more preferably approximately 8 to approximately 12, are necessary for a high distribution of the $1\alpha,24\text{-(OH)}_2\text{—V.D}_3$ in the oil phase and, in turn, the chemical stability of the $1\alpha,24\text{-(OH)}_2\text{—V.D}_3$.

Third, regarding the factors behind the physical stability of the cream composition, in particular, the separation of the oil phase and the aqueous phase under heating (or under heat load) or under centrifugation load, the present inventors found that the composition of the solid oil component and liquid oil component constituting the oil phase was important. That is, they found that, to keep the cream composition in a cream state even when placed under such stringent conditions, the ratio of the solid oil component to the liquid oil component in the oil phase (i.e., solid oil component/liquid oil component: ratio by weight) preferably should be approximately 2 or more.

In general, for example, to ensure a good feeling upon application to the skin, for example, to reduce the stickiness, the method of increasing the proportion of the liquid oil component has been often used. The inventors surprisingly discovered that by increasing the proportion of the solid oil component, in particular by making the weight ratio of the solid oil component to the liquid oil component approximately 2 or more, the physical stability of the cream composition is improved.

Looking at the prior art from this viewpoint, the solid oil component in the formula for a cream composition disclosed in the specification of EP-A-0,129,003 comprising 20 parts by weight of beeswax and the liquid oil component consisted of 40 parts by weight of liquid paraffin and 1 part by weight of almond oil, for a total of 41 parts by weight, and therefore the weight ratio of the solid oil component to the liquid oil component was 0.5 or less. Further, the solid oil component in the formula for a cream composition disclosed in the specification of Japanese Unexamined Patent Publication (Kokai) No. 60-174705 consisted of 10 parts by weight of white petrolatum, 4 parts by weight of solid paraffin, 3 parts by weight of beeswax, and 2 parts by weight of stearic acid, for a total of 19 parts by weight, and the liquid oil component consisted of 25 parts by weight of liquid paraffin and 5 parts by weight of olive oil, for a total of 30 parts by weight, and therefore, the ratio of weight of the solid oil component to the liquid oil component was approximately 0.63. Further, the solid oil component in the formula for an emulsion type local composition disclosed in the specification of Japanese Unexamined Patent Publication (Kokai) No. 4-210903 consisted of 1.5 parts by weight of cetyl alcohol and 2.5 parts by weight of stearyl alcohol, for a total of 4 parts by weight, and the liquid oil component consisted of 4 parts by weight of liquid paraffin, and therefore, the weight ratio of the solid oil component to the liquid oil component was 1.

On the other hand, the solid oil component in the formulas of the cream compositions disclosed in the specifications of WO92/01454 and WO91/1280 consisted of 17 parts by weight of white petrolatum and 6 parts by weight of cetostearyl alcohol, for a total of 23 parts by weight, while the liquid oil component consisted of 5 parts by weight of liquid paraffin, and therefore, the weight ratio of the solid oil component to the liquid oil component was 4.6.

Fourth, regarding the causes of the feeling of the cream composition upon application, in general, to keep down the stickiness of the cream composition, the practice has been to keep the ratio of the oil phase as small as possible and to select a liquid oil component having a good feeling as the liquid phase component. In the case of the $1\alpha,24\text{-(OH)}_2\text{—V.D}_3$ cream composition the present invention, however, it is necessary to make the liquid oil component ⅓ or less of the oil phase component from the viewpoint of the physical stability as mentioned above, and therefore, it is difficult to use the above general technique.

On the other hand, in general, as the liquid oil component, use is made of many hydrocarbons and esters as mentioned above. Surprisingly, however, the present inventors found that, when using squalane as the liquid oil component, a superior feeling was obtained upon application compared with the case of use of, for example, liquid paraffin as used in the prior art, e.g., the stickiness at the time of application was reduced and there was much less shininess of the applied location.

Consequently, in accordance with the present invention, there are provided a $1\alpha,24\text{-(OH)}_2\text{—V.D}_3$ cream composition comprising (a) a therapeutically effective amount of $1\alpha,24\text{-(OH)}_2\text{—V.D}_3$, (b) an oil phase component including
  (i) a solid oil component comprising 5 to 20 parts by weight of white petrolatum and 5 to 15 parts by weight of higher alcohols and
  (ii) a liquid oil component comprising 3 to 10 parts by weight of squalane, (c) an aqueous phase component, and (d) 2.5 to 7.5 parts by weight at least two surfactants, wherein the $1\alpha,24\text{-(OH)}_2\text{—V.D}_3$ cream composition has a weight ratio of the solid oil component to the liquid oil component (i.e., solid oil component/liquid oil component) of at least approximately 2, the higher alcohols are composed of stearyl alcohol and cetyl alcohol, the weight ratio of the stearyl alcohol to the higher alcohols (i.e., stearyl alcohol/higher alcohols) is approximately 0.65 to approximately 0.9, at least 50% by weight of the surfactants is at least one surfactant having an HLB value of approximately 5 or less, and the HLB value of the surfactants as a whole is approximately 8 to approximately 18 and a pharmaceutical preparation for treatment of psoriasis comprising that cream composition.

BRIEF DESCRIPTION OF THE DRAWINGS

The present invention will now be described in further detail with reference to the drawing of FIG. 1 which shows a test apparatus used in Reference Test 4.

BEST MODE FOR CARRYING OUT THE INVENTION

Figure 1:
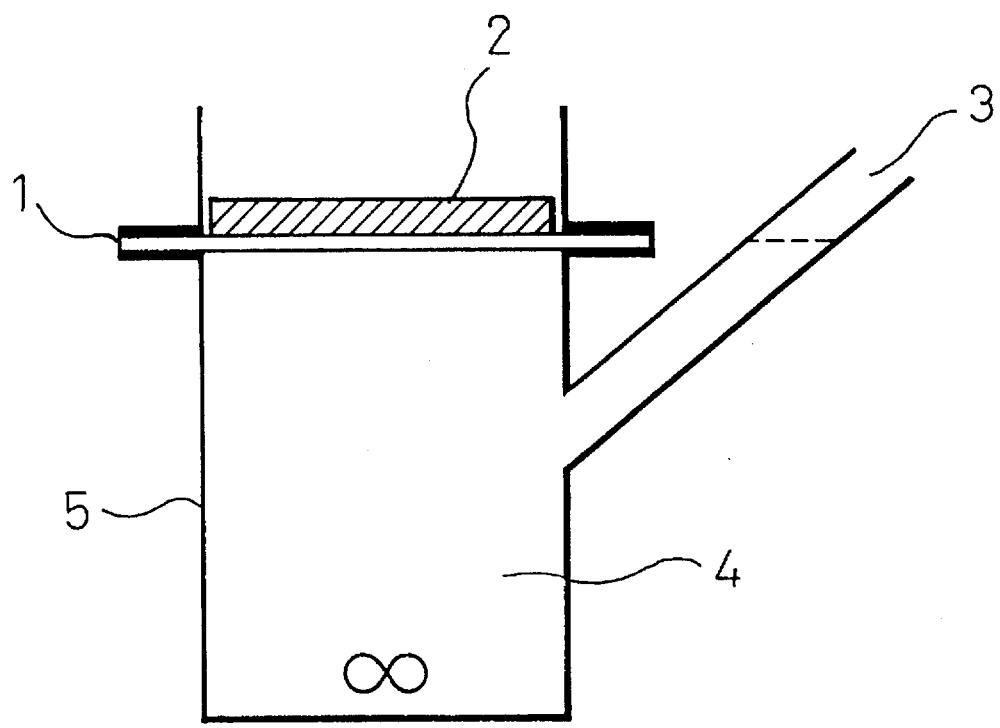

The oil phase component constituting the $1\alpha,24\text{-}(OH)_2\text{—}V.D_3$ cream composition of the present invention is composed of a solid oil component comprising 5 to 20 parts by weight of white petrolatum and 5 to 15 parts by weight of higher alcohols and a liquid oil component comprising 3 to 10 parts by weight of squalane.

The white petrolatum of the present invention is one obtained by bleaching and refining a mixture of hydrocarbons obtained from oil. For the specifications, use is made of the specifications set forth in, for example, the Japan Pharmacopoeia. In particular, one which is high in purity is desirable in terms of the stability of the $1\alpha,24\text{-}(OH)_2\text{—}V.D_3$. For example, one having a peroxide value of 0.5 or less is desirable. The higher alcohols according to the present invention are mixtures of cetyl alcohol and stearyl alcohol. The ratio by weight of the stearyl alcohol in the mixture as the whole is from approximately 0.65 to approximately 0.9. Particularly preferably, mention may be made of the range of approximately 0.7 to approximately 0.9, in particular, preferably approximately 0.70 to approximately 0.85. The skin permeability tends to increase along with the gradual increase of the stearyl alcohol from cetyl alcohol alone. When the weight ratio of the stearyl alcohol exceeds approximately 0.7, the skin permeability increases suddenly. It becomes maximum with stearyl alcohol alone. When the ratio exceeds approximately 0.9, however, there is a tendency for the physical stability of the emulsion, in particular, the physical stability under heating, to deteriorate.

The generally marketed cetyl alcohol and stearyl alcohol are sometimes not pure products. For example, what is called cetyl alcohol sometimes is a mixture of approximately 0.7 of cetyl alcohol and approximately 0.3 of stearyl alcohol. Further, what is called cetostearyl alcohol sometimes is a mixture of approximately 0.6 to approximately 0.3 of cetyl alcohol and approximately 0.4 to approximately 0.7 of stearyl alcohol. The cetyl alcohol and stearyl alcohol in the present invention indicate the pure products. The ratios of mixture of the same are calculated based on these.

Further, the squalane of the present invention is a saturated hydrocarbon obtained by reducing hydrocarbons obtained from the liver oil of, for example, deep sea sharks. The specifications used are those for example established in the Cosmetic Ingredient Standards.

For the oil phase component of the present invention, in addition to the above-mentioned white petrolatum, higher alcohols, and squalane, it is possible to add other solid oil components and liquid oil components. The amounts added should be ones in the range in which one of the objects of the present invention, for example, the physical stability, is maintained. An amount of not more than 1/10 part by weight of the solid oil component of the present invention is preferable in that it enables a suitable hardness of the cream composition to be maintained. As the liquid oil components, mention may be made of medium chain-length fatty acid triglyceride, diisopropyl adipate, isopropyl myristate, and other esters. The amounts of these liquid oil components added should be ones in the range in which one of the objects of the present invention, for example, the skin permeability of the $1\alpha,24\text{-}(OH)_2\text{—}V.D_3$, is maintained. An amount of not more than 3/10 part by weight of the squalane is preferable in that it enables a good skin permeability of the $1\alpha,24\text{-}(OH)_2\text{—}V.D_3$ to be maintained.

The surfactants of the present invention comprises two or more types of surfactants, the total of which is 2.5 to 7.5 parts by weight of the cream composition as a whole. Further, at least 50% by weight of the surfactants are at least one surfactant having an HLB value of approximately 5 or less. The HLB value of the surfactants as a whole is approximately 8 to approximately 18. More preferably, it is approximately 8 to approximately 12.

As the at least one surfactant having an HLB value of approximately 5 or less constituting at least 50% by weight of the surfactants used in the present invention, mention may be made of at least one surfactant selected from the group comprising for example sorbitan monooleate, sorbitan monostearate, sorbitan sesquioleate, sorbitan trioleate, glyceryl monostearate, glyceryl monooleate, propylene glycol monostearate, etc. The remaining surfactants are not particularly limited, so long as the overall HLB value is approximately 8 to approximately 18, more preferably approximately 8 to approximately 12, but, for example, mention may be made of at least one surfactant selected from the group comprising polyoxyethylene (30 or 40 or 60) sorbitantetraoleate, polyoxyethylene (60) hardened castor oil, sorbitan monolaurate, sorbitan monopalmitate, polyoxyethylene (20) sorbitan monolaurate, polyoxyethylene (20) sorbitan monopalmitate, polyoxyethylene (20) sorbitan monostearate, polyoxyethylene (20) sorbitan monooleate, polyoxyethylene (10) monolaurate, polyoxyethylene (23 or 25 or 30) cetyl ether, etc.

An antioxidant may be added to the oil phase component of the cream composition of the present invention. As the antioxidant, butylhydroxytoluene, butylhydroxyanisole, dl-$\alpha$-tocopherol, etc., more preferably dl-$\alpha$-tocopherol, is added. The amount of addition is usually 0.001 to 5.0 parts by weight, more suitably 0.01 to 3.0 parts by weight.

A humectant, preservative, chelating agent, buffer, etc. can be added to the aqueous phase component of the $1\alpha,24\text{-}(OH)_2\text{—}V.D_3$ cream composition of the present invention. As the humectant, mention may be made of propylene glycol, glycerine, sorbitol, etc. The addition amount is 1 to 20 parts by weight, more preferably 2 to 15 parts by weight. As the preservative, mention may be made of methyl hydroxybenzoate, propyl hydroxybenzoate, mixtures of the same, and other hydroxybenzoate; chlorobutanol; monothioglycerol; sorbic acid, potassium sorbate; benzyl alcohol, etc. The addition amount is 0.001 to 10.0 parts by weight, more preferably 0.01 to 5.0 parts by weight. As the chelating agent, mention may be made of citric acid, sodium citrate; sodium edetate, etc. The addition amount is 0.001 to 5.0 parts by weight, more preferably 0.01 to 3.0 parts by weight. As the buffer, mention may be made of disodium hydrogenphosphate, sodium dihydrogenphosphate, etc. These are added in the ratio of weight necessary for adjusting the pH of the water phase components to 6.5 to 8.0.

As the $1\alpha,24\text{-}(OH)_2\text{—}V.D_3$ of the active ingredient of the present invention, among the $1\alpha,24(R)\text{-}(OH)_2\text{—}D_3$ and $1\alpha,24(S)\text{-}(OH)_2\text{—}V.D_3$, $1\alpha,24(R)\text{-}(OH)_2\text{—}D_3$ is preferable due to its superiority in pharmacological activity. Further, among the types of $1\alpha,24(R)\text{-}(OH)_2\text{—}V.D_3$, crystals are preferable in terms of the purity. For example, use may be made of the one-hydrate of the same.

The amount of $1\alpha,24\text{-}(OH)_2\text{—}V.D_3$ included in the $1\alpha,24\text{-}(OH)_2\text{—}V.D_3$ cream composition of the present invention is the amount therapeutically effective for the skin ailment for which it is applied. It usually is in the range of approximately 0.00005 to approximately 0.01% by weight in terms of the concentration in the cream composition.

The $1\alpha,24\text{-(OH)}_2\text{—V.D}_3$ cream composition of the present invention is produced by the ordinary method of heating and dissolving the necessary amount of the active ingredient $1\alpha,24\text{-(OH)}_2\text{—V.D}_3$ along with the surfactant in the oil phase component, mixing thereof with the aqueous phase component heated in an emulsifier, then emulsifying the components to obtain a homogeneous emulsion which is then cooled.

The $1\alpha,24\text{-(OH)}_2\text{—V.D}_3$ cream composition of the present invention can be used for the treatment of, for example psoriasis vulgaris, pustular psoriasis, psoriasis guttata, erythrodermic psoriasis, psoriasis arthropathica, inveterate psoriasis, and other various types of psoriasis. The amount administered differs according to the degree of severity of the disease etc., but a cream composition having a concentration of $1\alpha,24\text{-(OH)}_2\text{—V.D}_3$ of 100 µg to 0.1 µg/g is preferably applied one to several times a day.

Therefore, provision is made of a $1\alpha,24\text{-(OH)}_2\text{—V.D}_3$ cream composition which has a $1\alpha,24\text{-(OH)}_2\text{—V.D}_3$ active ingredient having an excellent skin permeability and improved chemical stability and, further, which is superior in physical stability as a cream composition and excellent in the feeling upon application to the skin. The present invention is extremely significant in that it provides for clinical use a $1\alpha,24\text{-(OH)}_2\text{—V.D}_3$ cream composition which is equivalent in pharmacological activity with a water-free ointment of the same content. Further, it is extremely significant in providing for clinical use a $1\alpha,24\text{-(OH)}_2\text{—V.D}_3$ cream composition which is not only excellent in skin permeability and pharmacological activity, but is also excellent in the feeling at the time of application to the skin, superior in physical stability as an emulsion, and excellent in the chemical stability of the active ingredient $1\alpha,24\text{-(OH)}_2\text{—V.D}_3$.

EXAMPLES

The present invention will now be explained further with reference to Examples, although the present invention is not limited to these Examples. First, an explanation will be made of the various types of test methods used in the Examples.

1. Test Method of Feeling Upon Application

Samples of the cream composition were coated on the forearms of five healthy test subjects by the subjects themselves. The subjects then evaluated each of the (1) stickiness at time of coating, (2) easy of vanishing of whiteness, and (3) stickiness and shininess after application—giving them five rankings. The amount of the cream composition applied was 50 mg. This was applied to a 3 cm×3 cm square portion of the forearm. In the five-rank evaluation, a higher rank was given for the better evaluation.

2. Test Method of Physical Stability of Cream Composition 2-1. Test Under Centrifugation A 1 g sample of the cream composition was taken in a centrifugation tube, spun in a centrifuge at approximately 4000 rpm for 3 hours, then taken out and observed as to the outer appearance of the cream composition to determine if the oil phase and the water phase separated.

2-2. Test Under Heat Load (Heating Test)

A 1 g sample of the cream composition was taken in a glass sample tube which was then hermetically sealed and stored in a 60° C. constant temperature tank. The external appearance of the cream composition was observed over time to check for the separation of the oil phase and water phase.

3. Test Method for Comparing Skin Permeability of $1\alpha,24\text{-(OH)}_2\text{—V.D}_3$ from Cream Composition For this test, use was made of the test apparatus shown in FIG. 1. In the figure, 1 shows excised skin, 2 a sample of the cream composition, 3 a sampling port, 4 a reservoir solution, and 5 a cell. For the skin, use was made of skin cut off from a dilapidated Wistar rat (full skin=including stratum corneum, epidermis, and dermis). For the reservoir solution, use was made of Hanks buffer (pH=7.4) plus 10% bovine fetal serum. The cell was kept at 37° C., the sample cream composition was applied onto the top surface of the skin to 5 mg/cm², the reservoir solution was sampled from the sampling port after a constant time, and the $1\alpha,24\text{-(OH)}_2\text{—V.D}_3$ in the reservoir solution was assayed by HPLC. (For the method of assay, see below.)

Note that the test was performed with the concentration of 50 µg/g of the $1\alpha,24\text{-(OH)}_2\text{—V.D}_3$ in the cream made.

4. Test Method of Chemical Stability of $1\alpha,24\text{-(OH)}_2\text{—V.D}_3$ in Cream Composition The $1\alpha,24\text{-(OH)}_2\text{—V.D}_3$ in the cream composition was assayed by the method described below.

A 400 mg amount of the cream composition was taken in a centrifugation tube. To this were added 30 mcl of an internal standard solution (130 mcg prednisolon/ethanol ml), 3 ml of dichloromethane, and 0.5 ml of saturated saline. The mixture was shaken for 10 minutes, then centrifuged for 10 minutes at 3000 rpm, while cooling to 5° C. The bottom layer, or dichloromethane layer, was taken and part was poured into a HPLC column to assay the $1\alpha,24\text{-(OH)}_2\text{—V.D}_3$. The HPLC conditions were as described below:

Column: Inertsil 5C18 4.6* 250 mm

Column temperature: 40° C.

Eluent: n-hexane/EtOH (89/11)

Flow rate: 1.2 ml/min

5. Test Method of Pharmacological Activity of $1\alpha,24\text{-(OH)}_2\text{—V.D}_3$ Cream Composition For the psoriasis animal model, the activity of $1\alpha,24\text{-(OH)}_2\text{—V.D}_3$ in suppressing cell growth was evaluated using ODC (ornithine decarboxylase) activity as a marker of the cell growth activity. That is, the skin of hairless mice was treated with TPA (12-O-tetradecanoylphorbol-13-acetate) to accelerate the growth of the epidermic cells. $1\alpha,24\text{-(OH)}_2\text{—V.D}_3$ cream composition was administered to this and the suppression of growth was evaluated by measuring the ODC activity. Explaining this in more detail, first, 10 nmol of TPA was applied to a 3×3 cm section of the back of the hairless mice to accelerate the growth of epidermic cells. Next, 50 mg of the test sample (cream composition) were applied to the same location in the case of the test group (nothing applied for the control group). After five hours, the skin of the administered location was cut off and the ODC activity was measured by the method of Chiba, K., et al (Cancer Res., 44: 1387 to 1391 (1984)). The ratio of the ODC activity of the test group to that of the control group was found and used as the rate of suppression. This was used as the indicator of the pharmacological activity of the $1\alpha,24$-$(OH)_2$—$V.D_3$ cream composition.

6. Measurement of Rate of Distribution of $1\alpha,24$-$(OH)_2$—$V.D_3$ in Cream Composition in Oil and Aqueous Phases A 10 g amount of the cream composition was taken and separated by centrifugation (15000 g×240 min) into the oil phase and aqueous phase. The $1\alpha,24$-$(OH)_2$—$V.D_3$ in the aqueous phase was assayed by the method according to the above-mentioned section 4 and the rate of distribution in the oil and water phase of the $1\alpha,24$-$(OH)_2$—$V.D_3$ was calculated.

Example 1

The solid oil component (component 2 to 4), liquid oil component (component 5), surfactants (component 6 to 8), antioxidant (component 10), and preservative (component 12) set forth in the following Table 1 were taken and mixed, then heated to 80° C. to make a homogeneous solution. To this was added the component 1 to make a homogeneous solution (solution A). On the other hand, a humectant (component 9), preservative (component 11), and buffers (component 13, 14) were added to water (component 15) to make a homogeneous solution (solution B). This was heated to 80° C. The solution A and solution B were mixed and emulsified in a vacuum emulsifier (made by Mizuho) to make a homogeneous emulsified composition which was then cooled to room temperature to obtain a white cream (Example 1).

TABLE 1

| Active ingredient | 1. $1\alpha,24$-$(OH)_2$—$V.D_3$ | 0.0002 part wt. |
|---|---|---|
| Solid oil component | 2. White petrolatum | 10 parts by weight |
| | 3. Stearyl alcohol | 8 parts by weight |
| | 4. Cetyl alcohol | 2 parts by weight |
| Liquid oil component | 5. Squalane | 5 parts by weight |
| Surfactant | 6. Glyceryl monostearate | 2.4 parts by weight |
| | 7. Polyoxyethylene (60) hardened castor oil | 0.8 part by weight |
| | 8. Polyoxyethylene (23) cetyl ether | 0.8 part by weight |
| Humectant | 9. Propylene glycol | 10 parts by weight |
| Antioxidant | 10. dl-α-tocopherol | 0.02 part by weight |
| Preservative | 11. Methyl hydroxybenzoate | 0.1 part by weight |
| | 12. Propyl hydroxybenzoate | 0.05 part by weight |
| Buffer | 13. Disodium hydrogenphosphate | q.s. (pH = 7.2) |
| | 14. Sodium dihydrogenphosphate | q.s. (pH = 7.2) |
| | 15. Refined water | q.s. |
| Total | | 100 parts by weight |

Control Example 1

In accordance with the formula disclosed in EP-A-0,129, 003, $1\alpha,24(R)$—$(OH)_2$—$V.D_3$ was dissolved in a mixture of 40 parts by weight of liquid paraffin and 1 part by weight of almond oil and the mixture was held at 80° C. To this was added 20 parts by weight of self-emulsifying beeswax along with 40 parts by weight of 80° C. water. The mixture was emulsified and cooled to obtain a $1\alpha,24$-$(OH)_2$—$V.D_3$ cream composition (Control Example 1).

Control Example 2

A $1\alpha,24$-$(OH)_2$—$V.D_3$ cream composition of the following formula was obtained in accordance with the method disclosed in the specification of Japanese Unexamined Patent Publication (Kokai) No. 60-174705 (Control Example 2):

| Additive | Comp. no. | Name of component | Ratio (wt. parts) |
|---|---|---|---|
| Active ingredient | 1 | $1\alpha,24(R)$-$(OH)_2$—$V.D_3$ | 0.0002 |
| Solid oil component | 2 | White petrolatum | 10 |
| | 3 | Solid paraffin | 4 |
| | 4 | Beeswax | 3 |
| | 5 | Stearic acid | 2 |
| Liquid oil component | 6 | Liquid paraffin | 25 |
| | 7 | Olive oil | 5 |
| Surfactant | 8 | Polyoxyethylene cetyl ether | 2 |
| | 9 | Sorbitan monostearate | 1 |
| Humectant | 10 | Polyethylene glycol 1500 | 2 |
| | 11 | Preservative | q.s. |
| Others | 12 | Refined water | 45 |
| Total | | | 100 |

Control Example 3

A $1\alpha,24$-$(OH)_2$—$V.D_3$ cream composition (Control Example 3) of the following formula disclosed in the specification of Japanese Unexamined Patent Publication (Kokai) No. 4-210903 was produced in accordance with the description of the specification:

| Additive | Comp. no. | Name of component | Ratio (wt. parts) |
|---|---|---|---|
| Active ingredient | 1 | $1\alpha,24(R)$-$(OH)_2$—$V.D_3$ | 0.0002 |
| Solid oil component | 2 | Cetyl alcohol | 1.5 |
| | 3 | Stearyl alcohol | 2.5 |
| Liquid oil component | 4 | Liquid paraffin | 4 |
| Surfactant | 5 | Sorbitan monostearate | 2.0 |
| | 6 | Aracel 165 (reg. trademark) | 4.0 |
| | 7 | Polysorbate 60 (reg. trademark) | 1.0 |
| Humectant | 8 | Propylene glycol | 5 |
| | 9 | Sorbitol solution | 2 |
| Antioxidant | 10 | Butylhydroxyanisole | 0.05 |
| Stabilizer | 11 | Oisodium edetate | 0.01 |
| Preservative | 12 | Propyl hydroxybenzoate | 0.05 |
| | 13 | Methyl hydroxybenzoate | 0.18 |
| Others | 14 | Refined water | q.s. |
| Total | | | 100 |

Control Example 4

The $1\alpha,24$-$(OH)_2$—$V.D_3$ cream composition (Control Example 4) of the following formula disclosed in the specifications of WO92/01454 and 91/1280 was prepared in accordance with the description of that specification:

| Additive | Comp. no. | Name of component | Ratio (wt. parts) |
|---|---|---|---|
| Active ingredient | 1 | $1\alpha,24(R)\text{-}(OH)_2\text{—}V.D_3$ | 0.0002 |
| Solid oil component | 2 | White petrolatum | 17 |
|  | 3 | Cetostearyl alcohol | 6 |
| Liquid oil component | 4 | Liquid paraffin | 5 |
| Surfactant | 5 | Cetomacrogol | 3 |
| Humectant | 6 | Propylene glycol | 3 |
| Preservative | 7 | Chloroallylhexaminium chloride | 0.05 |
| Buffer | 8 | Disodium hydrogenphosphate | 0.2 |
|  | 9 | Sodium dihydrogenphosphate | 0.01 |
| Others | 10 | Refined water | q.s |
| Total |  |  | 100 |

Control Example 5

The $1\alpha,24\text{-}(OH)_2\text{—}V.D_3$ water-free ointment (Control Example 5) of the following formula was obtained in accordance with the method disclosed in the specification of Japanese Examined Patent Publication (Kokoku) No. 3-68009.

| Additive | Comp. no. | Name of component | Ratio (wt. parts) |
|---|---|---|---|
| Active ingredient | 1 | $1\alpha,24(R)\text{-}(OH)_2\text{—}V.D_3$ | 0.0002 |
| Substrate | 2 | White petrolatum | 95 |
|  | 3 | Liquid paraffin | 4.5 |
| Solvent | 4 | Diisopropyl adipate | 0.5 |
| Total |  |  | 100 |

Reference Test 1

Test of Chemical Stability of $1\alpha,24\text{-}(OH)_2\text{—}V.D_3$ in Cream Composition of Example 1

Use was made of the cream compositions of Example 1 and Control Examples 1 and 2, the cream composition of Example 1 but with beeswax used instead of white petrolatum (Control Example 6), the cream composition of Example 1, but with stearic acid used instead of the white petrolatum (Control Example 7), the cream composition of Example 1 but with lanolin used instead of white petrolatum (Control Example 8), and the cream composition of Example 1, but with stearic acid used instead of the higher alcohols of Example 1 (Control Example 9). The cream compositions were packaged in aluminum tubes and stored at 40° C. for six months and then the residual rate of $1\alpha,24\text{-}(OH)_2\text{—}V.D_3$ to the initial rate (%) was found by the Test Method 4. The results are shown in Table 2.

TABLE 2

| Sample (components of solid oil component) |  | Residual rate of $1\alpha,24\text{-}(OH)_2\text{—}V.D_3$ (%) |
|---|---|---|
| Example 1 | (white petrolatum, stearyl alcohol, cetyl alcohol) | 96 |
| Control Example 1 | (beeswax) | 73 |
| Control Example 2 | (white petrolatum, solid paraffin, beeswax, stearic acid) | 62 |
| Control Example 6 | (beeswax, stearyl alcohol, cetyl alcohol) | 75 |
| Control Example 7 | (stearic acid, stearyl alcohol, cetyl alcohol) | 51 |
| Control Example 8 | (lanolin, stearyl alcohol, cetyl alcohol) | 68 |
| Control Example 9 | (white petrolatum, stearic acid) | 57 |

The above results show that waxes (Control Examples 1, 2, and 6), lanolin (Control Example 8), and other naturally derived components, probably because of impurities, and higher fatty acids (Control Examples 7 and 9), probably due to their acidity, are unsuitable in terms of the stability of the $1\alpha,24\text{-}(OH)_2\text{—}V.D_3$. As a result, it is learned that white petrolatum and higher alcohols are suitable as the solid oil components for a $1\alpha,24\text{-}(OH)_2\text{—}V.D_3$ cream composition.

Reference Test 2

Test of Feeling of Cream Composition of Example 1 Upon Application to Skin

The Test Method 1 was followed using five test subjects to compare the feel and look of the cream composition upon application. For the sample, use was made of the cream compositions of Example 1 and Control Examples 1, 2, 3, and 4 and an agent comprised of Example 1 except for using liquid paraffin in place of squalane (Control Example 10) and an agent comprised of Example 1 except for using medium chain-length fatty acid triglyceride instead of squalane (Control Example 11). The results are shown in Table 3.

TABLE 3

| Sample (components of liquid oil component) |  | Stickiness after application | Vanishing of whiteness | Shininess after application |
|---|---|---|---|---|
| Example 1 | (squalane) | 5 | 5 | 5 |
| Control Example 1 | (liquid paraffin, almond oil) | 1 | 1 | 1 |
| Control Example 2 | (liquid paraffin, olive oil) | 3 | 2 | 1 |
| Control Example 3 | (liquid paraffin) | 5 | 4.5 | 4.5 |
| Control Example 4 | (liquid paraffin) | 4.5 | 5 | 4.5 |
| Control Example 10 | (liquid paraffin) | 4.5 | 5 | 4 |
| Control Example 11 | (neutral fatty acid triglyceride) | 5 | 5 | 5 |

Note: Figures are averages for five subjects.

From Table 3, it is learned that the cream compositions of Control Examples 1 and 2, which include large amounts of liquid paraffin as the liquid oil component, do not easily vanish when the white cream compositions are applied on the skin and are both sticky and shiny at the time of application, so the feel and look at the time of application are remarkably inferior.

As opposed to this, compared with Control Examples 1 and 2, the cream compositions of Control Examples 3, 4, and 10, which include liquid paraffin, are relatively improved in terms of the stickiness after application, the vanishing of the whiteness, and shininess after application, but are still not sufficient in these regards. On the other hand, these problems are solved when the liquid paraffin is replaced by squalane or medium chain-length fatty acid triglyceride (Example 1, Control Example 11).

Reference Test 3

Test of Physical Stability of Cream Composition of Example 1

A test was made of the physical stability of the cream composition under centrifugation and heating in accordance with the Test Method 2. For the samples, use was made of the cream compositions of Example 1, Control Examples 1, 2, 3, and 4, the cream compositions of Example 1 but with the 5 parts by weight of squalane made 10 parts by weight (Example 2), the cream composition of Example 1 but with the 10 parts by weight of white petrolatum, 8 parts by weight of stearyl alcohol, 2 parts by weight of cetyl alcohol, and 5 parts by weight of squalane made 7 parts by weight, 4 parts by weight, 1 part by weight, and 4 parts by weight (Example 3), the cream composition of Example 1 but with the 5 parts by weight of squalane made 13 parts by weight (Control Example 12), the cream composition of Example 1 but with the 10 parts by weight of white petrolatum, 8 parts by weight of stearyl alcohol, 2 parts by weight of cetyl alcohol, and 5 parts by weight of squalane made 6 parts by weight, 4 parts by weight, 1 part by weight, and 10 parts by weight (Control Example 13), and the cream composition of Example 1 but with the 8 parts by weight of stearyl alcohol and 2 parts by weight of cetyl alcohol made 10 parts by weight and 0 part by weight (Control Example 14). For the evaluation under centrifugation, it was determined if the oil and aqueous phases had separated after the samples were taken out and, for the evaluation under heating, the number of days until separation of oil and aqueous phases was measured. The results are shown in Table 4.

From Table 4, it is shown that when considering the relationship between the ratio of weight of the solid oil component and liquid oil component in the samples with the physical stability, it is preferable in terms of physical stability that the ratio be at least 2. Even though the ratio is 2 or more, however, Control Example 14, which includes higher alcohols as the solid oil component, was somewhat inferior in terms of physical stability under heating.

TABLE 4

| Sample (components of solid oil component/liquid oil component; ratio) | | Separation of oil and water under centrifugation | No. of days required for separation of oil and water under heating |
|---|---|---|---|
| Ex. 1 | [white petrolatum, stearyl alcohol, cetyl alcohol/squalane; 4] | No | 4 days |
| Ex. 2 | [white petrolatum, stearyl alcohol, cetyl alcohol/squalane; 2] | No | 4 days |
| Ex. 3. | [white petrolatum, stearyl alcohol, cetyl alcohol/squalane; 3] | No | 4 days |
| Con. Ex. 1 | [Beeswax/liquid paraffin, almond oil; 0.49] | Yes | 0.5 day |

TABLE 4-continued

| Sample (components of solid oil component/liquid oil component; ratio) | | Separation of oil and water under centrifugation | No. of days required for separation of oil and water under heating |
|---|---|---|---|
| Con. Ex. 2 | [White petrolatum, solid paraffin, beeswax, stearic acid/liquid paraffin, olive oil; 0.63] | Yes | 1 day |
| Con. Ex. 3 | [Cetyl alcohol, stearyl alcohol/liquid paraffin; 1] | Yes | 2 days |
| Con. Ex. 4 | [White petrolatum, stearyl alcohol/liquid paraffin; 4.6] | No | 4 days |
| Con. Ex. 12 | [White petrolatum, stearyl alcohol, cetyl alcohol/squalane; 1.54] | No | 2 days |
| Con. Ex. 13 | [White petrolatum, stearyl alcohol, cetyl alcohol/squalane; 1.1] | Yes | 1 day |
| Con. Ex. 14 | [White petrolatum, stearyl alcohol/squalane; 4] | No | 2.5 days |

Reference Test 4

Test of Skin Permeability of $1\alpha,24\text{-}(OH)_2\text{---}V.D_3$ from Cream Composition of Example 1

A test was made of the skin permeability of $1\alpha,24\text{-}(OH)_2\text{---}V.D_3$ from the cream composition in accordance with the Test Method 3. Table 6 shows the relative rate of permeation (%) of samples using as 100 the amount of the $1\alpha,24\text{-}(OH)_2\text{---}V.D_3$ passing from the water-less ointment of Control Example 5 to a reservoir side after three hours.

TABLE 5

| Sample | Higher alcohol composition of sample | |
|---|---|---|
| | Stearyl alcohol (parts by weight) | Cetyl alcohol (parts by weight) |
| Example 4 | 9 | 1 |
| Example 5 | 7 | 3 |
| Control Example 14 | 10 | 0 |
| Control Example 15 | 6 | 4 |
| Control Example 16 | 5 | 5 |
| Control Example 17 | 4 | 6 |
| Control Example 18 | 3 | 7 |
| Control Example 19 | 2 | 8 |
| Control Example 20 | 1 | 9 |
| Control Example 21 | 0 | 10 |

Note that for the samples, use was made of the cream compositions of Example 1 and Control Example 1 to 4 and, also, the cream compositions of Control Examples 10 and 11 (see Reference Test 2) and Examples 4 and 5 and Control Examples 14 to 21 comprising Example 1 but with the weight ratios of stearyl alcohol and cetyl alcohol changed as shown in Table 5. Further, in the test, the concentration of the $1\alpha,24\text{-}(OH)_2\text{---}V.D_3$ in the cream compositions and ointments was made 50 µg/g.

TABLE 6

| | Ratio of weight of stearyl alcohol/higher alcohols among higher alcohols of solid oil component | Relative rate of permeation (%) |
|---|---|---|
| Control Example 5 | (—) | 100 |
| Example 1 | (0.8) | 98 |
| Example 4 | (0.9) | 98 |
| Example 5 | (0.7) | 96 |
| Control Example 1 | (—) | 25 |
| Control Example 2 | (—) | 47 |
| Control Example 3 | (0.625) | 44 |
| Control Example 4 | (0.5) | 51 |
| Control Example 10 | (0.8)* | 97 |
| Control Example 11 | (0.8)** | 63 |
| Control Example 14 | (1.0) | 98 |
| Control Example 15 | (0.6) | 76 |
| Control Example 16 | (0.5) | 51 |
| Control Example 17 | (0.4) | 44 |
| Control Example 18 | (0.3) | 39 |
| Control Example 19 | (0.2) | 40 |
| Control Example 20 | (0.1) | 33 |
| Control Example 21 | (0) | 29 |

*Use of liquid paraffin as liquid oil component.
**Use of medium chain-length fatty acid triglyceride as liquid oil component.

From these results, it is learned that the cream composition of the present invention as shown in Example 1 was superior in skin permeability compared with the active $V.D_3$ cream compositions disclosed in the past as shown in Control Examples 1 to 4 and that the skin permeability of $1\alpha,24\text{-}(OH)_2\text{---}V.D_3$ in the cream composition of the present invention is dependent on the composition of the higher alcohol and increases remarkably when the ratio of stearyl alcohol in the whole is at least about 0.7. Note that while the cream composition of Control Example 14 is superior in skin permeability, it is insufficient in the physical stability as a cream composition, as explained in Reference Test 3. Further, the cream composition of Control Example 10 is inferior to the cream composition of the present invention in terms of feel and look (see Reference Test 2, Table 3), but is sufficiently superior in permeability, while Control Example 11 is equal to the cream composition of the present invention in terms of feel and look (see Reference Test 2, Table 3), but is much more inferior in skin permeability.

Reference Test 5

Test of Pharmacological activity of Cream Composition of Example 1

Table 7 shows the results of comparative tests on the pharmacological activity of samples the same as in Reference Test 4, that is, creams (but with a content of the base in the cream composition made 2 μg/g) and ointments (but with a content of the base in the ointment made 2 μg/g), in accordance with Test Method 5. These are shown by the relative rates of inhibition (%) using as 100 the rate of inhibition of ODC activity of the water-free ointment of Control Example 5.

TABLE 7

| Sample | Relative rate of inhibition (%) |
|---|---|
| Control Example 5 | 100 |
| Example 1 | 102 |
| Example 4 | 105 |
| Example 5 | 96 |
| Control Example 1 | 12 |
| Control Example 2 | 15 |
| Control Example 3 | 9 |

TABLE 7-continued

| Sample | Relative rate of inhibition (%) |
|---|---|
| Control Example 4 | 23 |
| Control Example 10 | 101 |
| Control Example 11 | 29 |
| Control Example 14 | 103 |
| Control Example 15 | 66 |
| Control Example 16 | 60 |
| Control Example 17 | 48 |
| Control Example 18 | 41 |
| Control Example 19 | 43 |
| Control Example 20 | 41 |
| Control Example 21 | 39 |

From Table 7, it is learned that in an animal model of psoriasis, the cream composition of the present invention (Examples 1, 4, and 5) exhibits a pharmacological activity of $1\alpha,24\text{-}(OH)_2\text{---}V.D_3$ equivalent to the water-free ointment of Control Example 5. Further, these results show that the cream composition of the present invention is dependent on the skin permeability shown in Reference Test 4 and is superior in terms of pharmacological activity as well.

Reference Test 6

Test of Rate of Distribution in Oil and Aqueous Phase of $1\alpha,24\text{-}(OH)_2\text{---}V.D_3$ in Cream Composition of Example 1

The rate of distribution in the oil and aqueous phase of the $1\alpha,24\text{-}(OH)_2\text{---}V.D_3$ in the cream composition was found in accordance with Test Method 6. As the samples, use was made of the cream compositions of Examples 1, 2, 3, 4, and 5 and Control Examples 2, 3, and 4 and, also, samples of Example 1 with the surfactants changed as shown in Table 8.

TABLE 8

| Sample | Surfactants | HLB value | Parts by weight |
|---|---|---|---|
| Ex. 6 | Sorbitan monostearate | 3 | 2 |
| | Polyoxyethylene (60) hydrogenated castor oil | 14 | 1 |
| | Polyoxyethylene (23) cetyl ether | 18 | 1 |
| Ex. 7 | Sorbitan monostearate | 5 | 2.4 |
| | Polyoxyethylene (60) hydrogenated castor oil | 14 | 0.8 |
| | Polyoxyethylene (23) cetyl ether | 18 | 0.8 |
| Ex. 8 | Sorbitan monostearate | 4.3 | 1.2 |
| | Glyceryl monooleate | 3 | 1.2 |
| | Polyoxyethylene (60) hydrogenated castor oil | 14 | 0.8 |
| | Polyoxyethylene (23) cetyl ether | 18 | 0.8 |
| Con. Ex. 22 | Sorbitan monostearate | 3 | 1.6 |
| | Polyoxyethylene (60) hydrogenated castor oil | 14 | 1.2 |
| | Polyoxyethylene (23) cetyl ether | 18 | 1.2 |
| Con. Ex. 23 | Sorbitan monostearate | 3 | 1 |
| | Polyoxyethylene (60) hydrogenated castor oil | 14 | 1.5 |
| | Polyoxyethylene (23) cetyl ether | 18 | 1.5 |
| Con. Ex. 24 | Polyoxyethylene (23) cetyl ether | 18 | 5 |
| Con. Ex. 25 | Polyoxyethylene (20) sorbitan monoleate | 15 | 6 |
| Con. Ex. 26 | Polyoxyethylene (20) sorbitan monoleate | 15 | 4 |
| | Glyceryl monoleate | 3 | 2 |

Table 9 shows the rates of distribution in the aqueous phase (%) of these samples and the residual rates (%) of the $1\alpha,24\text{-}(OH)_2\text{---}V.D_3$ when the samples are packaged in aluminum tubes and stored at 40° C. for 6 months.

TABLE 9

| Samples | [Surfactant of HLB 5 or less/surfactant as whole (parts by weight)] | Rate of distribution in aqueous phase (%) | Residual rate of $1\alpha,24\text{-}(OH)_2\text{—}V.D_3$ (%) |
|---|---|---|---|
| Ex. | | | |
| 1 | (60%) | 0.8 | 96 |
| 2 | (60%) | 0.9 | 95 |
| 3 | (60%) | 0.8 | 94 |
| 4 | (60%) | 1.0 | 93 |
| 5 | (60%) | 0.7 | 94 |
| 6 | (50%) | 1.2 | 92 |
| 7 | (60%) | 1.1 | 93 |
| 8 | (60%) | 1.0 | 92 |
| Control Ex. | | | |
| 2 | (about 33%) | 1.8 | 62 |
| 3 | (about 85%) | 0.9 | 88 |
| 4 | (0%) | 1.7 | 84 |
| 22 | (40%) | 1.7 | 75 |
| 23 | (20%) | 1.6 | 81 |
| 24 | (0%) | 2.3 | 79 |
| 25 | (0%) | 2.0 | 84 |
| 26 | (about 33%) | 1.5 | 87 |

From Table 9, it is clear that having at least 50% by weight of the surfactants be lipophilic surfactants having an HLB value of less than approximately 5 contributes to the greater distribution of the $1\alpha,24\text{-}(OH)_2\text{—}V.D_3$ in the cream composition to the oil phase and as a result contributes to the stability of the $1\alpha,24\text{-}(OH)_2\text{—}V.D_3$.

Reference Test 7

Examples Showing Limits of Amounts of Oil Phase and Surfactants in Cream Composition The cream compositions of the following Examples 9 and 10 were prepared by changing the amounts of the oil phase and surfactants of Example 1. The properties of these cream compositions are shown in Table 10. In both cases, excellent cream compositions like in Example 1 were obtained.

Example 9

| Additive | Comp. no. | Name of component | Amount (wt. part) |
|---|---|---|---|
| Active ingredient | 1 | $1\alpha,24\text{-}(OH)_2\text{—}V.D_3$ | 0.0002 |
| Solid oil component | 2 | White petrolatum | 5 |
| | 3 | Stearyl alcohol | 4 |
| | 4 | Cetyl alcohol | 1 |
| Liquid oil component | 5 | Squalane | 3 |
| Surfactant | 6 | Glyceryl monostearate | 1.5 |
| | 7 | Polyoxyethylene (60) hydrogenated castor oil | 0.5 |
| | 8 | Polyoxyethylene cetyl ether | 0.5 |
| Humectant | 9 | Propylene glycol | 10 |
| Antioxidant | 10 | Dl-α-tocopherol | 0.02 |
| Preservative | 11 | Methyl hydroxybenzoate | 0.1 |
| | 12 | Propyl hydroxybenzoate | 0.05 |
| Buffer | 13 | Disodium hydrogenphosphate | q.s. (pH = 7.2) |
| | 14 | Sodium dihydrogenphosphate | |
| | 15 | Refined water | q.s. |
| Total | | | 100 |

Example 10

| Additive | Comp. no. | Name of component | Amount (wt. part) |
|---|---|---|---|
| Active ingredient | 1 | $1\alpha,24\text{-}(OH)_2\text{—}V.D_3$ | 0.0002 |
| Solid oil component | 2 | White petrolatum | 20 |
| | 3 | Stearyl alcohol | 12 |
| | 4 | Cetyl alcohol | 3 |
| Liquid oil component | 5 | Squalane | 10 |
| Surfactant | 6 | Glyceryl monostearate | 4 |
| | 7 | Polyoxyethylene (60) hydrogenated castor oil | 1.5 |
| | 8 | Polyoxyethylene cetyl ether | 2.0 |
| Humectant | 9 | Propylene glycol | 10 |
| Antioxidant | 10 | dl-α-tocopherol | 0.02 |
| Preservative | 11 | Methyl hydroxybenzoate | 0.1 |
| | 12 | Propyl hydroxybenzoate | 0.05 |
| Buffer | 13 | Disodium hydrogenphosphate | q.s. (pH = 7.2) |
| | 14 | Sodium dihydrogenphosphate | |
| | 15 | Refined water | q.s. |
| Total | | | 100 |

TABLE 10

| | Ex. 9 | Ex. 10 | Ex. 1 |
|---|---|---|---|
| Feeling upon application | No different from Ex. 1 | No different from Ex. 1 | — |
| Physical stability | | | |
| (Under centrifugation) | No separation | No separation | No separation |
| (Under heating) | Separation after 4 days | Separation after 4 days | Separation after 4 days |
| Skin permeability (relative rate of permeation) | 98% | 98% | 98% |
| Pharmacological activity (relative rate of inhibition) | 101% | 97% | 105% |
| Rate Of distribution in aqueous phase | 1.0% | 0.9% | 0.8% |
| Chemical stability (residual rate of $1\alpha,24\text{-}(OH)_2\text{—}V.D_3$) | 96% | 96% | 96% |

Reference Test 8

Cream compositions comprising Example 1 but including 0.00005 part by weight (Example 11) and 0.01 part by weight (Example 12) of $1\alpha,24\text{-}(OH)_2\text{—}V.D_3$ instead of 0.0002 part by weight were prepared. The skin permeabilities were compared with that of a water-free ointment (same formula as Control Example 5) of the same concentration in accordance with the Test Method 3, whereupon it was found that the skin permeabilities were approximately 99%.

Reference Test 9

Test of Addition of Liquid Oil Component

Cream compositions were prepared in which 1, 1.5, and 2 parts by weight of diisopropyl adipate were added to the 5 parts by weight of the liquid oil component squalane of Example 1 (Example 13, Example 14, and Control Example 27). The properties of the cream compositions of Examples 13 and 14 (feel and look, physical stability, skin permeability, pharmacological activity, ratio of distribution in the oil and aqueous phases, chemical stability, etc.) were substantially the same as those of the cream composition of Example 1, but when the skin permeability of Control Example 27 was compared with the cream composition of Example 1 by the Test Method 3, it was found to be an inferior relative permeation of 80%. It is possible to add esters in addition to the squalane as the liquid oil component, but if the solubility of the $1\alpha,24$-$(OH)_2$—$V.D_3$ rises too much, the skin permeability falls, so it is estimated that the amount is limited to about 30% of the squalane.

Reference Test 10

Effect on Ratio of Mixture of Higher Alcohol on Skin Permeability When Using Hydrocortisone Acetate as Base Cream compositions including 0.25 part by weight of hydrocortisone acetate and components other than the base made the same as in Examples 1, 4, and 5 and Control Examples 14 to 21 were tested by the Test Method 3 to compare the skin permeabilities of the hydrocortisone acetate. Unlike in the case of $1\alpha,24$-$(OH)_2$—$V.D_3$, the permeability was almost completely unrelated to the weight ratio of the stearyl alcohol and cetyl alcohol. The discovery of the present invention that the skin permeability of $1\alpha,24$-$(OH)_2$—$V.D_3$ is largely dependent on the components and proportions of the higher alcohol was made possible by the fact that the content here was extremely small. The conventionally known steroid creams would probably show that something like the present test would be impossible.

INDUSTRIAL APPLICABILITY

As explained above, the cream composition of the present invention is not only superior in the skin permeability of the $1\alpha,24$-$(OH)_2$—$V.D_3$ contained, but also is excellent in the chemical stability of the active ingredient, excellent in the feeling at the time of application to the skin, and excellent in the physical stability as an emulsion, and therefore, enables effective application of $1\alpha,24$-$(OH)_2$—$V.D_3$ as a cream composition to the skin etc.

We claim:

1. A $1\alpha,24$-$(OH)_2$-cholecalciferol cream composition for psoriasis comprising:
   (a) a therapeutically effective amount to treat psoriasis of $1\alpha,24$-$(OH)_2$-cholecalciferol,
   (b) an oil phase component comprising:
      (i) a solid oil component comprising white petrolatum and a mixture of higher alcohols, wherein the white petrolatum is present in an amount of from 5 to 20 parts by weight based on 100 parts by weight of the total cream composition, and the mixture of higher alcohols is present in an amount of from 5 to 15 parts by weight based on 100 parts by weight of the total cream composition, and
      (ii) a liquid oil component, wherein the liquid oil component comprises squalane, wherein the squalane is present in an amount of from 3 to 10 parts by weight based on 100 parts by weight of the total cream composition,
   (c) an aqueous phase component, and
   (d) at least two surfactants present in an amount of from 2.5 to 7.5 parts by weight based on 100 parts by weight of the total cream composition,
   wherein the weight ratio of the solid oil component to the liquid oil component is at least approximately 2; the liquid component is 1/3 or less of the oil phase component; the mixture of higher alcohols is stearyl alcohol and cetyl alcohol; the weight ratio of stearyl alcohol to the total amount of stearyl alcohol and cetyl alcohol is approximately 0.7 to 0.9; at least 50% by weight of the surfactants is at least one surfactant having an HLB value of approximately 5 or less, and the HLB value of the surfactants as a whole is approximately 8 to 18.

2. The $1\alpha,24$-$(OH)_2$-cholecalciferol cream composition according to claim 1, wherein said surfactant having an HLB value of approximately 5 or less is selected from the group consisting of sorbitan monooleate, sorbitan monostearate, sorbitan sesquioleate, sorbitan trioleate, glyceryl monostearate, glyceryl monooleate, and propylene glycol monostearate.

3. The $1\alpha,24$-$(OH)_2$-cholecalciferol cream composition according to claims 1 or 2, wherein $1\alpha,24$-$(OH)_2$-cholecalciferol is present in an amount ranging from 0.00005 to 0.01% by weight.

4. A method for treating psoriasis comprising the step of topically administering to an area of a patient in need of such treatment a $1\alpha,24$-$(OH)_2$-cholecalciferol cream composition comprising:
   (a) a therapeutically effective amount of $1\alpha,24$-$(OH)_2$-cholecalciferol,
   (b) an oil phase component comprising:
      (i) a solid oil component comprising white petrolatum and a mixture of higher alcohols, wherein the white petrolatum is present in an amount of from 5 to 20 parts by weight based on 100 parts by weight of the total cream composition, and the mixture of higher alcohols is present in an amount of from 5 to 15 parts by weight based on 100 parts by weight of the total cream composition, and
      (ii) a liquid oil component, wherein the liquid oil component comprises squalane, wherein the squalane is present in an amount of from 3 to 10 parts by weight based on 100 parts by weight of the total cream composition,
   (c) an aqueous phase component, and
   (d) at least two surfactants present in an amount of from 2.5 to 7.5 parts by weight based on 100 parts by weight of the total cream composition,
   wherein the weight ratio of the solid oil component to the liquid oil component is at least approximately 2; the liquid component is 1/3 or less of the oil phase component; the mixture of higher alcohols is stearyl alcohol and cetyl alcohol; the weight ratio of stearyl alcohol to the total amount of stearyl alcohol and cetyl alcohol is approximately 0.7 to 0.9; at least 50% by weight of the surfactants is at least one surfactant having an HLB value of approximately 5 or less, and the HLB value of the surfactants as a whole is approximately 8 to 18.

5. The method of treating psoriasis according to claim 4, wherein said surfactant having an HLB value of approximately 5 or less is selected from the group consisting of sorbitan monooleate, sorbitan monostearate, sorbitan sesquioleate, sorbitan trioleate, glyceryl monostearate, glyceryl monooleate, and propylene glycol monostearate.

6. The method for treating psoriasis according to claim 4, wherein $1\alpha,24$-$(OH)_2$-cholecalciferol is present in an amount ranging from 0.00005 to 0.01% by weight.

* * * * *